(12) United States Patent
Policker et al.

(10) Patent No.: US 6,480,737 B1
(45) Date of Patent: Nov. 12, 2002

(54) FIELD DELIVERY SAFETY SYSTEM USING DETECTION OF ATYPICAL ECG

(75) Inventors: Shai Policker, Tzur-Moshe; Yuval Mika, Zichron-Yaacov, both of (IL); David Prutchi, Lake Jackson, TX (US); Itzhak Shemer, Zichron-Yaacov (IL)

(73) Assignee: Impulse Dynamics NV, Curacao (NL)

( * ) Notice: Subject to any disclaimer, the term of this patent is extended or adjusted under 35 U.S.C. 154(b) by 0 days.

(21) Appl. No.: 09/914,547

(22) PCT Filed: Dec. 28, 2000

(86) PCT No.: PCT/IL00/00873
§ 371 (c)(1),
(2), (4) Date: Aug. 28, 2001

(87) PCT Pub. No.: WO01/49367
PCT Pub. Date: Jul. 12, 2001

Related U.S. Application Data

(60) Provisional application No. 60/173,422, filed on Dec. 29, 1999.

(51) Int. Cl.[7] .................................................. A61N 1/00
(52) U.S. Cl. .......................................................... 607/2
(58) Field of Search ........................................ 607/1–28

(56) References Cited

U.S. PATENT DOCUMENTS

| | | |
|---|---|---|
| 4,387,717 A | 6/1983 | Brownlee et al. |
| 5,738,105 A | 4/1998 | Kroll |
| 5,978,707 A | 11/1999 | Krig et al. |
| 6,233,487 B1 | 5/2001 | Mika et al. |
| 6,261,280 B1 | 7/2001 | Houben et al. |
| 6,263,242 B1 * | 7/2001 | Mika et al. |
| 6,292,693 B1 | 9/2001 | Darvish et al. |

FOREIGN PATENT DOCUMENTS

| | | |
|---|---|---|
| WO | WO 97/25098 | 7/1997 |
| WO | WO 98/10831 | 3/1998 |
| WO | WO 98/10832 | 3/1998 |
| WO | WO 99/27994 | 6/1999 |
| WO | WO 00/57952 | 10/2000 |
| WO | WO 01/00137 | 1/2001 |
| WO | WO 01/13992 | 3/2001 |
| WO | WO 01/87134 | 11/2001 |

* cited by examiner

Primary Examiner—Scott M. Getzow
(74) Attorney, Agent, or Firm—Feaster & Company Ltd.

(57) ABSTRACT

Apparatus for applying a non-excitatory signal to a heart, comprising: at least one electrode, a power source, a wide-field ECG sensor that receives a wide-field ECG signal containing contributions from non-local sized portions of the heart, a controller for selectively electrifying said at least one electrode with a non-excitatory signal from said power source, and a safety filter that inhibits said electrifying responsive to said wide-field ECG signal.

34 Claims, 1 Drawing Sheet

FIELD DELIVERY SAFETY SYSTEM USING DETECTION OF ATYPICAL ECG

RELATED APPLICATIONS

This application is a U.S. national filing of PCT Application No. PCT/IL00/00873, filed Dec. 28, 2000.

This application is related to and claims the benefit under 35 USC 119(e) of U.S. Ser. No. 60/173,422 filed on Dec. 29, 1999, the disclosure of which is incorporated herein by reference.

FIELD OF THE INVENTION

The present relates to inhibition of delivery of inappropriate controlling currents to a heart.

BACKGROUND

The application of a non-excitatory field to the heart, in order to modify its contractility and/or have another desirable controlling effect on the heart is described, for example in PCT/IL97/00012, the disclosure of which is incorporated herein by reference.

Such non-excitatory signals can cause, in some cases, an arrhythmia, which may be potentially fatal, for example if it is applied to excitable tissue. The signal is applied, in some devices, in a time window determined based on a locally sensed depolarization event. Such a window will also tend to prevent pro-arrhythmia effects, at least in some cases. However, if an arrhythmia exists, the applied non-excitatory signal can cause a further arrhythmia.

However, in spite of these and other safety measures that may be applied, there remains the danger that an applied non-excitatory signal will inadvertently cause or interact with an arrhythmia.

SUMMARY OF THE INVENTION

An aspect of some embodiments of the invention relates to using a wide-field ECG signal to determine when to inhibit the application of a non-excitatory control signal (ETC). The application of an ETC signal may be prevented or an ETC signal being applied may be stopped and/or modified. In an exemplary embodiment of the invention, the ETC signal is designed to increase contractility, decrease contractility, change an activation profile (e.g., conduction velocity or heart rate) and/or prevent propagation of arrhythmia.

In an exemplary embodiment of the invention, the wide-field ECG signal contains contributions from a significant portion of the heart and is used to determine if the heart, as a whole (or a significant portion thereof) is experiencing a normal activation profile (e.g., one for which the ETC signal is suitable). In an exemplary embodiment of the invention, the wide-field ECG includes contributions from two or more chambers and/or from a heart portion having a surface area of over 3, 5 or 15 $cm^2$.

In an exemplary embodiment of the invention, the wide-field ECG is compared to one or more templates of suitable or unsuitable heart ECGs. In an exemplary embodiment of the invention, the ECG comprises a trace of the ECG from the start of the beat until when the ETC signal is applied. Alternatively other methods of matching an ECG signal to stored signal parameters are used.

An aspect of some embodiments of the invention relates to a method of acquiring and/or maintaining a "normal" template of heart ECG activation In an exemplary embodiment of the invention, a plurality of ECG traces are accumulated for heart cycles. The ECG traces may be accumulated separately for different states, for example, for machine-paced cycles and for autonomous-paced cycles. In an exemplary embodiment of the invention, a dispersion (and/or other variation-related parameter) of the ECG traces is calculated. Possibly, the dispersion is used when matching an ECG trace to the template, to determine if the trace "fits" the template or not.

In an exemplary embodiment of the invention, the template is continuously updated, possibly also with "abnormal" ECG traces. In an exemplary embodiment of the invention, this type of updating allows the template to track changes in the normal activation of the heart.

Alternatively or additionally, when a template is not matched for a considerable period of time (e.g. 120 beats), it is dropped. Revival may be automatic, for example if the template matches at least a threshold amount over a threshold period. Alternatively or additionally, revival may be manual, for example, by a physician that programs an ETC controller that delivers the non-excitatory signal.

There is thus provided in accordance with an exemplary embodiment of the invention, apparatus for applying a non-excitatory signal to a heart, comprising:

at least one electrode;

a power source;

a wide-field ECG sensor that receives a wide-field ECG signal containing contributions from non-local sized portions of the heart;

a controller for selectively electrifying said at least one electrode with a non-excitatory signal from said power source; and a safety filter that inhibits said electrifying responsive to said wide-field ECG signal. Optionally, said wide-field ECG sensor detects electric field contributions from at least two heart chambers. Alternatively or additionally, said wide-field ECG detects electric field contributions from an area of at least 5 cm2 of the heart. Alternatively or additionally, said wide-field ECG detect electric field contribution from all area of at least 15 cm2 of the heart.

In an exemplary embodiment of the invention, said wide-field ECG sensor detects electric field contributions from at least one quarter of a heart chamber. Alternatively or additionally, said wide-field ECG sensor detects electric field contributions from at least one third of a heart chamber.

In an exemplary embodiment of the invention, said wide-field ECG sensor detects electric field contributions from parts of the heart that are expected to be activated prior to said electrifying. Alternatively or additionally, said wide-field ECG sensor detects electric field contributions from parts of the heart that are expected to be activated after to said electrifying. Alternatively or additionally, said wide-field ECG sensor includes at least one component shared with a sensor used for timing said electrifying. Optionally, said wide-field ECG sensor shares said at least one electrode.

In an exemplary embodiment of the invention, said non-excitatory signal increases a contractility of at least a portion of said heart.

In an exemplary embodiment of the invention, said safety filter includes a template matcher that matches said ECG trace to at least one template. Optionally, said template matcher matches said ECG trace to at least one template suitable for a paced heart and at least one template suitable for an unpaced heart. Alternatively or additionally, said at least one template includes at least two templates, each designated for different heart rates. Alternatively, said at least one template includes a single template suitable for multiple heart rates.

In an exemplary embodiment of the invention, said at least one template includes at least two templates, each designated for a different non-excitatory signal. Alternatively or additionally, said at least one template includes at least two templates, each designated for a wide-field ECG sensing area. Alternatively or additionally, said at least one template includes an ECG portion corresponding to a period between a right ventricle pacing or sensing event and a time for application of a non-excitatory signal. Alternatively or additionally, said at least one template is continuously updated. Optionally, said at least one template is updated to be a weighted average of a current template and a current ECG signal. Alternatively, said at least one template is updated with both normal and abnormal ECG signals.

In an exemplary embodiment of the invention, said filter ignores templates that did not match for a considerable period of time. Alternatively or additionally, said filter prevents said electrification from starting.

In an exemplary embodiment of the invention, said filter stops an ongoing electrification from continuing. Alternatively or additionally, said filter is configured to prevent arrhythmia to be caused by said non-excitatory signal. Alternatively or additionally, said filter is configured to prevent inefficient non-excitatory signal to be applied to said heart.

In an exemplary embodiment of the invention, said wide-field ECG sensor comprises two electrode portions spaced apart at least 3 centimeters. Optionally, said wide-field ECG sensor comprises two electrode portions spaced apart at least 5 centimeters. Alternatively or additionally, at least one of said two electrode portions is adapted to be placed distanced from the heart. Alternatively or additionally, at least one of said two electrode portions is adapted to be in contact with the heart's inner surface. Alternatively or additionally, at least one of said two electrode portions is adapted to be in contact with the heart's outer surface. Alternatively or additionally, at least one of said two electrode portions is adapted to float in the heart's volume. Alternatively or additionally, said two electrodes are mounted on a same elongate lead.

There is also provided in accordance with an exemplary embodiment of the invention, a method of determining if to inhibit the application of a non-excitatory signal to the heart, comprising:

detecting a non-local ECG trace;

determining if said trace indicates a normal activation of the heart; and inhibiting the application of a non-excitatory signal responsive to a negative determination of said trace.

BRIEF DESCRIPTION OF THE FIGURES

Non-limiting exemplary embodiments of the invention will be described in following description of exemplary embodiments, read in conjunction with the accompanying figures. Identical structures, elements or parts that appear in more than one of the figures are labeled with a same or similar numeral in all the figures in which they appear.

DETAILED DESCRIPTION OF SOME EMBODIMENTS OF THE INVENTION

Figure 1:
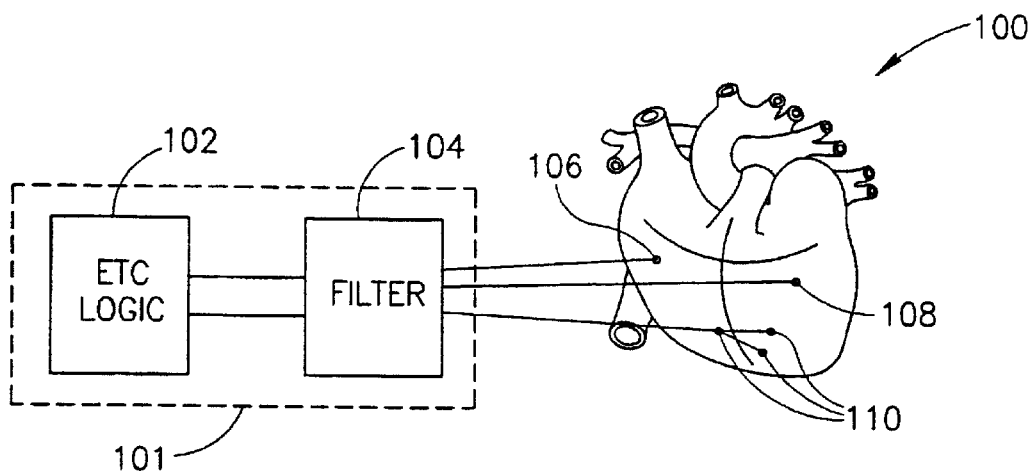
FIG. 1 is a schematic illustration of an ETC controller including a safety filter in accordance with an exemplary embodiment of the present invention.

FIG. 1 is a schematic illustration of an ETC controller 101 including a safety filter 104 in accordance with an exemplary embodiment of the present invention. ETC controller 101 includes an ETC logic module 102 that generates a non-excitatory signal to be applied to a heart 100 via one or more electrodes, such as electrodes 106 and 108. Apparatus for such generation of non-excitatory control signals and various types of such signals, are described, for example, in PCT/IL97/00012 and in PCT publications WO 97/25098, WO 98/10831, WO 98/10832 and U.S. patent application Ser. No 09/260,769, the disclosures of which are incorporated herein by reference.

As used herein the term non-excitatory is used to describe a pulse that does not generate a new propagating action potential, but may modify an existing or future potential. This behavior may be, for example, a result of the pulse amplitude, frequency application location and/or pulse envelope, and generally also depends on the timing of the pulse application. It is noted that a single pulse may have excitatory and non-excitatory parts. For example a 100 ms pacing pulse, may cease to have a pacing effect after 20 ms and have real non-excitatory effects after 40 ms.

In an exemplary embodiment of the invention, module 102 generates a contractility enhancing signal. However, if such a signal is applied at an inappropriate timing relative to the refractory period of the heart tissue to which it is applied, the signal will be excitatory and generate a propagating action potential. This action potential can be the cause of a fatal arrhythmia.

In an exemplary embodiment of the invention, a safety filter 104 is provided, to inhibit ETC signals that might cause arrhythmia. In an exemplary embodiment of the invention, as described below, filter 104 operates by comparing a currently acquired a non-local ECG trace with allowed values for such a trace. Such a non-local ECG trace while possibly less suitable for detecting local events, may be used to detect area-wide activation profiles, or at least whether such a profile is normal or not. Optionally, the trace is acquired using a plurality of ECG electrodes 110. This comparison serves as an overall reasonableness test. If the test fails, meaning that the heart cycle is not proceeding "normally", the ETC is not applied. Optionally, as described below, a template of allowed traces is used to match the trace.

In an exemplary embodiment of the invention, filter 104 is provided as a watchdog, that is applied separately from other logic used to decide whether to apply an ETC signal and what that signal should be. Alternatively, the logic of filter 104 is integrated with the logic of ETC logic 102.

In an exemplary embodiment of the invention, filter 104 is a logic filter, in that it inhibits a "go-ahead" signal for delivering an ETC signal or it provides a "no-ETC" signal to ETC logic 102. Alternatively, filter 104 is a power filter, that prevents the current applied by ETC logic 102 from reaching electrodes 106 and 108. Optionally, this current is used for operating filter 104. Therefore, filter 104 may optionally be provided as a stand alone device or upgrade, alternatively to being provided integrally with ETC logic 102 in a single casing.

Figure 2:
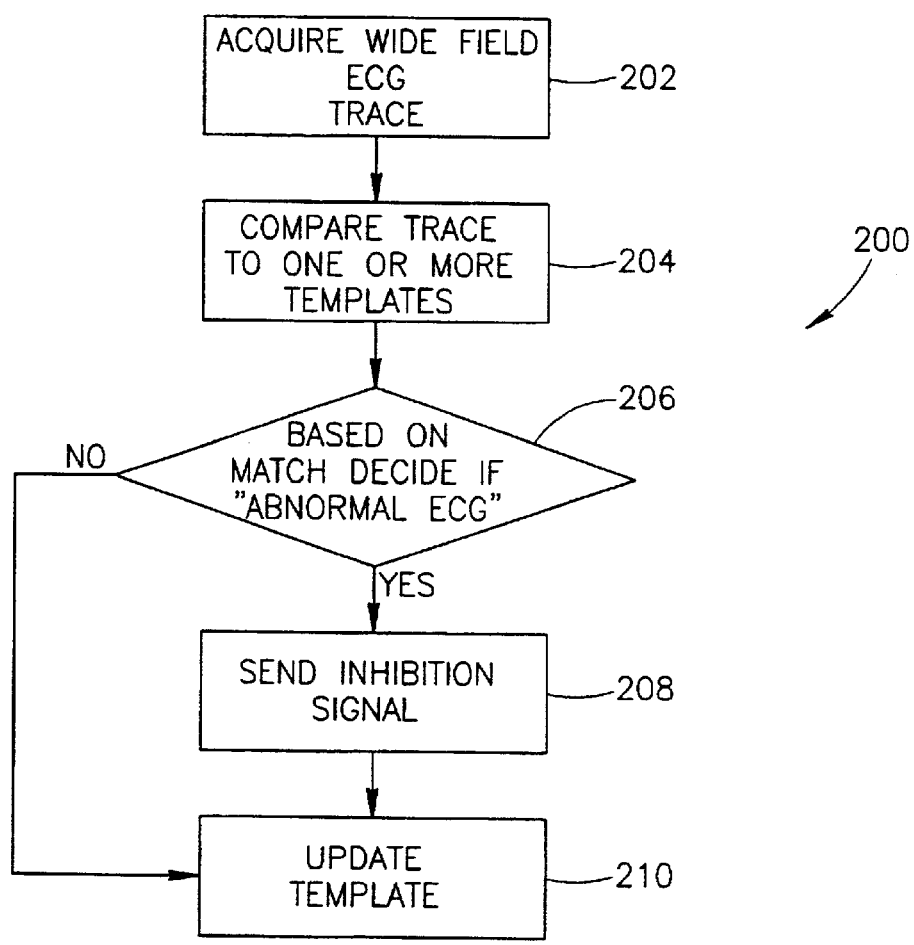
FIG. 2 is a flowchart of a method of determining if to inhibit an ETC signal, in accordance wit an exemplary embodiment of the invention.

FIG. 2 is a flowchart 200 of a method of determining if to inhibit an ETC signal, in accordance with an exemplary embodiment of the invention.

At 202, a wide field ECG trace is acquired using ECG electrodes 110. Electrodes 110 may be dedicated electrodes or they may be part of controller 101, for example, spaced apart electrification electrodes, that are read as ECG electrodes, for example using methods known in the art or pairs of ECG sensing electrodes used by ETC logic 102, or a set comprising an ECG sensing electrode and a ETC electrification electrode. Optionally, the wide-field ECG sensor has shared components with ETC logic 102, for example, one or more electrodes, switch(es) and/or a processing circuit.

In an exemplary embodiment of the invention, different electrodes are placed on different heart chambers. In an exemplary embodiment of the invention, one of the electrodes comprises the casing of controller 101. Alternatively or additionally, the electrodes are spaced-apart ring electrodes on a catheter. Alternatively or additionally, at least one of the ECG electrodes is located on an electrification or ECG electrode lead, distanced a short distance from the heart. Alternatively, other implantable electrode configurations may be used.

Alternatively or additionally, electrodes 110 are external electrodes, for example, 12-lead ECG electrodes. Such external electrodes may communicate with filter 104 and/or ETC logic 102, using wired or wireless means, for example as known in the art. Alternatively, controller 101 may be an external controller, for example one used after cardiac-affecting surgery.

At 204, the acquired trace is compared to one or more templates. Alternatively, other matching methods, as described below may be used. The templates may include one or more "normal" templates, which indicate a suitable cardiac cycle and/or one or more "abnormal" templates, which indicate an abnormal cardiac cycle.

At 206, a decision is made to inhibit the ETC signal, based on the comparisons of 204. For example, if no "normal" template was matched or if an "abnormal" template was matched, an inhibition signal is generated to ETC logic 102 (208).

In an exemplary embodiment of the invention, the inhibition signal prevents an ETC signal from being applied to the heart, in this cycle. Alternatively or additionally, the inhibition signal is applied to a later cycle. Alternatively or additionally, a current ETC signal is terminated, at once, or with a suitable tailing end, as a result of detecting an abnormal cardiac condition. Alternatively or additionally, an ongoing sequence of ETC pulses is stopped or modified. In an exemplary embodiment of the invention, an ETC sequence to be applied to the heart can be defined to be conditional, with different sub-sequences being applied, depending on the detection of an abnormal condition. Optionally, the tailing end depends on the abnormal condition detected by the template matching, for example, the tailing end including a counter-arrhythmia signal.

In an exemplary embodiment of the invention, at least two templates are provided, one for matching a self-paced condition and one for matching an artificially paced condition. An indication may or may not be provided to filter 104, regarding which condition is current. If controller 101 and/or a pacemaker (not shown) can apply multiple pacing schemes, multiple templates may be provided, optionally at least to the extent that different pacing schemes have markedly different normal wide-field ECG traces. Optionally, filter 104 and/or controller 101 include an input for receiving various parameters that can affect "normal" activation, for example, the ingestion of a pharmaceutical or the continuing activity of a multi-cycle cardiac control sequence, that is expected to affect the heart in a known manner, for example, each stage of the sequence having a different normal ECG.

Alternatively or additionally, different ETC pulses and/or sequences may have different danger conditions and/or danger levels associated with them. In an exemplary embodiment of the invention, different templates and/or different matching parameters are used depending on the type of ETC signal to be applied and/or depending on the sensitivity of the patient and/or depending on the importance of actually applying an ETC pulse periodically, at least.

Alternatively or additionally, an ETC signal is selected to be applied based on which templates were matched and which not. In one example, a list of ETC pulses (with a similar, general function) is ordered in order of desirability of application. The most desirable ETC pulse whose "normal" template matches the current ETC trace is applied. Alternatively or additionally, if a sequence of ETC signals is to be applied, those signals that do not have a matching "normal" template, are inhibited. Optionally, ETC logic 102 may prevent the application of an ETC signal, if a previous or later (e.g., in same cycle) signal is inhibited, even if the instant ETC signal may be applied. This mechanism may be used to prevent partial application of sequences, where the partial sequence is not effective and/or possibly damaging.

Optionally, template matching is used to detect a change in the state of the heart, for example, the completion of a remodeling process or a transition from a sleep pattern to an exercise pattern. As such, the template matching of filter 104 may provide an input to ETC logic 102 and/or be mirrored in ETC logic 102.

Referring again to ECG electrodes 110, their placement may reflect contingency, for example, the placement location of local sensing and/or electrifying electrodes, or it may be selected to have a certain wide-filed view of the heart. In one example, one electrode is on the right ventricle and one on the left ventricle. In another example, one electrode is at each end of the heart. In another example, the electrodes are arranged in a grid, and selectively coupled to yield a desirable ECG trace. Different ECG traces may be sensed for different ETC signal applications and/or locations.

In an exemplary embodiment of the invention, the wide-field covers parts of at least two chambers, for example the two ventricles. Alternatively or additionally, the field covers a significant part of the left ventricle or of the right ventricle. Alternatively or additionally, the field is aimed to cover a portion of the heart that is known or expected to activate abnormally, for example the right atrium. Alternatively or additionally, the field is aimed to include contributions from two parts of the heart, whose activation order is expected to change as a result of abnormal activation. Optionally, multiple wide-area ECGs are sensed, for example for matching templates to multiple areas, for a single or multiple pulse applications. Alternatively or additionally, the size and/or location of the field may be varied as part of a calibration process, for example per patient, per condition to be careful of and/or per ETC signal type.

In an exemplary embodiment of the invention, the portion of the heart viewed includes an area that is expected to be activated (hopefully correctly) before the ETC signal is to be applied. Alternatively or additionally, the portion includes an area that is expected not to be activated before the ETC signal is to be applied. Alternatively or additionally, the portion includes an area that is expected to be activated just as or just before the ETC signal is to be applied. Exemplary areas that may be viewed include areas where incorrect conduction pathways exist. Alternatively or additionally, the area may include parts where a normal conduction and activation profile is expected.

Different ECG sensing areas will generally affect the content of templates that are considered "normal". Conversely, different sensing areas may be useful for detecting different types of potential arrhythmia, for example, for different ETC signals.

In an exemplary embodiment of the invention, the wide-field includes significant contribution from at least 3, 5, 10, 15 $cm^2$ or more of the heart's surface. Alternatively or additionally, the field width may be measured in percentages, for example, being at least 10%, 20%, 40% or 60% of the heart's muscle volume.

In an exemplary embodiment of the invention, the matching of a current ECG trace to previously stored ECG parameters is by template matching. In an exemplary embodiment of the invention, the template defines a portion of the ECG trace to be matched and one or more matching parameters define an allowed variation between the trace and the template.

In an exemplary embodiment of the invention, the portion of ECG trace used for the matching is selected to include contributions from the parts of the heart that are of interest. As noted above, in some cases, the part of the heart that is being viewed is expected not to have an activation, at least for some of the time.

In an exemplary embodiment of the invention, the wide field ECG sensor covers part of the right ventricle and part of the left ventricle (e.g., near the apex) and the temporal potion sensing used for the match is between a right ventricle sensing event and a latest reasonable left ventricle ETC application event. When the right ventricle is paced, the trace may start slightly after the pacing event. Optionally, the template also includes portions from after the application of the ETC signal.

In other examples, the trace includes parts of the atrial activation and/or SA pacing.

Alternatively or additionally, the temporal portion is selected to include parts of the trace that are expected to be less affected by normal changes in the heart's activation, such as exercise events and changes in heart rate. For example, the inter-beat period may not be included in the template.

In an exemplary embodiment of the invention, the template matching uses a Woody filter, in which the ECG trace is temporally shifted to find a maximum correlation with the template. Alternatively or additionally, dynamic time warping methods may be applied to allow the trace to be compressed or expanded. The trace may be allowed to be flexible or it may be require to be expanded or shrunk by a certain fixed factor or according to fixed rules (e.g., one part of ECG should shrink half as much as a second part). The template matching may be fixed or may use a floating point representation.

Alternatively or additionally, different templates may be provided for different heart rate conditions.

Although a template may be limited to one cardiac cycle, in some embodiments of the invention, a multi-cycle template is provided, for example to detect arrhythmia that are characterized by beat-to-beat variations or by a periodic behavior. In an exemplary embodiment of the invention, such a template includes multiple ECG trace portions. Alternatively, such a template includes only parts (same or different) from ECG traces of consecutive beats. Possibly, filter 104 compares only the relevant parts of the acquired ECG signal to the template. Possibly, the template is designed to match spaced apart beats (e.g., skip beats) and/or to compare averaged ECG traces to the template.

In an exemplary embodiment of the invention, the distance function used for calculating the difference between the trace and the template is a simple linear distance. Alternatively or additionally, some parts of the template may have different weight than other parts. Alternatively or additionally, at least some parts of the template may define an RMS, quadric or exponential distance function. Alternatively or additionally, time offsets also affect the matching score. Alternatively or additionally, energy scaling may also affect the score.

Optionally, some limitation is imposed on the allowed beat-to-beat variation. For example, two consecutive beats are expected to match or not match the template in substantially similar manners. Thus, consecutive beats in which one is different from the template in one way and the other is different in another way may be used to inhibit an ETC signal, even though they both match the template, within defined parameters.

The matching parameters may be defined depending on the type of matching performed. For example, the parameters may include only an allowed variation. Alternatively or additionally, the parameters may define a dispersion, that a set of consecutive beats must maintain (or be lower). Alternatively or additionally, the parameters may include a method of calculating the distance or different weights for different parts of the template. Alternatively or additionally, the parameters may define the type of matching to be performed, for example template or non-template.

In an exemplary embodiment of the invention, an initial template may be provided with controller 101. Alternatively, a short learning process may be applied when controller 101 is installed and/or recalibrated. In an exemplary embodiment of the invention, the learning process includes acquiring a plurality of relevant ECG traces from the patient and defining a template(s) based on the average trace and an allowed deviation based on the disparity between the traces. A human operator may view the traces and/or the template and reject and/or modify them. In some cases, a single template may need to be split into two due to the distribution of ECG traces in a patient. Such programming may be, for example, by wired connection, or by wireless connection of a programmer with controller 101.

In an exemplary embodiment of the invention, if a template is not matched for a considerable period of time, for example, 120 beats, 1200 beats or 12000 beats, the template is dropped. Such lack of use may imply that the activation of the heart changed enough so that what was once normal activation, is now abnormal activation. An alert may be generated to the patient and/or a physician, using means known in the art, or the status may be retrieved when controller 101 is next reprogrammed/debriefed.

In an exemplary embodiment of the invention, the templates are continuously updated (210). Optionally, even abnormal traces are used for updating "normal" templates. On the one hand, what was once considered abnormal may now be normal. On the other hand, if such abnormal beats are infrequent enough, they will not markedly affect the template. In addition, many arrhythmia will not be repetitive, so their effect is negligible. Optionally, ETC logic 102 provides an arrhythmia signal to filter 104, so filter 104 can ignore or otherwise take into account ECG traces that are detected by ETC logic 102 to be arrhythmia.

In an exemplary embodiment of the invention, the template is updated to be a weighted average of the current template and the instant ETC trace. Thus, old traces have a smaller weight than newer ones and the template can adapt to current conditions. Alternatively, other averaging or updating methods may be used.

In an exemplary embodiment of the invention, this type of template updating takes into account the long term effects of changes in the cardiac activation profile as a result of the ETC treatment and/or health changes. Also, the ETC application profile may change when the cardiac activity changes in time. For example, the template and/or template matching method may be used to select which ETC signal or sequence to apply and/or which anti-arrhythmia signal to apply.

In an exemplary embodiment of the invention, templates are stored as sequences of samples, that match the samples acquired by the wide-field ETC sensor. Alternatively or additionally, other template storage methods may be used.

Alternatively to template matching, other matching methods may be used, for example, feature based matching, where certain features of the ECG trace are searched for and compared in shape and/or relative position to a template (or set of features and distances otherwise stored).

In an exemplary embodiment of the invention, a filtering algorithm is applied by a real-time device. In such a device it is usually desirable to reduce the computational load and/or memory load. Optionally, the template should be matched as ECG samples are acquired. Table I lists an exemplary algorithm, in which T0 is, for example 17 ms and T1 is automatically calculated as shown in step 1. This algorithm is to be applied to an ETC device that paces or senses a right-ventricle activation and applies an ETC signal to the left ventricle. In operation, an INHIBIT signal is updated by thresholding the value of a mean-absolute-distance between the current ECG trace and the relevant template racing or sensing). If INHIBIT is active when the ETC signal is to be applied, the signal is inhibited. The template is updated using a pseudo-coherent averager that averages the last NumBeats traces (of sense type beats or of pace type beats).

TABLE I

1. Set T1 to be RV to LV time + worst-case ETC delay
2. Set T0 to be 10 samples (17 ms)
3. Set TH from GUI
4. Set updateOnInhibit from GUI (TRUE or FALSE)
5. Set staleNum = 120
6. Set NumBeats from GUI (default 4 and must be power of 2 in this implementation)
7. Set TemplatePace = vector zeros(T1) (vector of T1 zeros)
8. Set TemplateSense = vector zeros(T1) (vector of T1 zeros)
9. Set lastUpdatePace = 0
10. Set lastUpdateSense = 0;
11. Set Inhibit = 1
12. Set accTH = 0
13. Set MSE = 0;
14. Wait for Vpace or Vsense
15. Set Inhibit = 1
16. Set Invect = zeros(T1)
17. Set t=0;
18. Acquire new sample --> Invect(t)
19. t=t+1;
20. accTH = accTH+TH
21. if t>T0
22. A = Invect(t)
23. If Vpace
24. B = TemplatePace(t)
25. Else
26. B = TemplateSense(t)
27. EndIf
28. If A>B
29. MSE=MSE+A−B
30. Else
31. MSE=MSE+B−A
32. EndIf TABLE I-continued 33. If MSE<accTH
34. Set Inhibit=0
35. EndIf
36. EndIf
37. if CCM detected or t>T1
38. if Vpace & (INHIBIT == 0 | updateOnInhibit == TRUE)
39. if lastDetectedPace<staleNum
40. TemplatePace = =((NumBeats−1)*TemplatePace+Invect)/NumBeats
41. Else
42. TemplatePace = vector zeros(T1)
43. EndIf
44. Last DetectedPace = 0;
45. LastDetectedSense = LastDetectedSense+1
46. ElseIf INHIBIT == 0 | updateOnInhibit == TRUE
47. If lastDetectedSense<staleNum
48. TemplateSense = ((NumBeats−1)*TemplateSense+Invect)/NumBeats
49. Else
50. Templatesense = vector zeros(T1)
51. EndIf
52. LastDetectedSense = 0;
53. LastDetectedPace = LastDetectedPace+1
54. EndIf
55. Goto 11
56. ELSE
57. Goto 18
58. EndIf Although ETC logic 102 may operate independently of the existence of filter 104, in some embodiments of the invention, ETC logic 102 is modified to take the inhibition into account. ETC logic 102 maybe applying ETC signals to achieve a long term effect, an average increase in blood flow and/or control of other bodily parameters. By inhibiting some of the ETC signals, such goals may be confounded. In an exemplary embodiment of the invention, the rate of application of ETC pulses is increased to compensate for inhibited pulses. Alternatively or additionally, the ETC signal is inhibited (by ETC logic 102 and/or filer 104) for one or more cycles following a true inhibition (e.g., due to a detected arrhythmia), for example, based on the degree of template match or mismatch, based on preset values and/or based on a delay while at least a certain percentage of the cycles match an "abnormal" template. Alternatively or additionally, the treatment sequence may be changed, if, in the particular heart, the sequence cannot be reliably applied. Possibly, such changes are automatically performed by ETC logic 102. Alternatively, a human operator reads indications of lack of application from ETC logic 102 and modifies the programming accordingly.

It should be noted that calibration information, matching parameters and/or other operational parameters of filter 104 can be learned by experience, for example by tracking the effect of the operation (or lack thereof) of filter 104 on a same or a different patient.

Filter 104 is expected to detect various abnormal conditions, for example, some types of premature ventricular contractions (PVC). In an exemplary embodiment of the invention, the arrhythmic condition to be detected comprises a beat from a non-sinus source that reaches the left-ventricle activation sensor slightly before (e.g., 10–20 ms) or slightly after the activation from the right ventricle reaches it. Alternatively or additionally, other safety mechanisms may be used to inhibit ETC signals, for example, one or more of:

(a) the detection of noise on local sensing ECG channels, for example, a right-ventricle channel;

(b) detecting a PVC using a right-heart sequence detector;

(c) detecting a left ventricle event during a right heart AV segment;

(d) detecting an abnormally short AV delay;

(e) detecting beats conducted from an atrium, especially a tachyarrhythmic atrium; and (f) inhibiting ETC signals for several cycles after a current ETC signal is inhibited and/or after an arrhythmia is detected.

Some of these mechanisms and/or mechanisms for determining a timing window during which an ETC pulse may be safely and/or usefully applied to a heart are described in U.S. patent application Ser. Nos. 09/276,460, 09/378,776, 09/572,482 and 09/338,649, and in PCT application Nos. PCT/IL00/00321 and PCT/IL00/00493 and PCT publication WO 00/57952, the disclosures of which are incorporated herein by reference.

Optionally, the templates are used to associate different locally sensed danger conditions (and/or sequences) with wide-field ECG signals, for example, for later use. Alternatively or additionally, windowing parameters for applying ECG signals may be associated with wide-field ECG templates.

Although the above application has focused on ETC signals, in some embodiments of the invention, filter 104 is used to inhibit excitatory signals generated by controller 101. In an exemplary embodiment of the invention, controller 101 may generate an excitatory signal which is not expected to cause an arrhythmia. However, due to an abnormal activation of the heart, the ETC signal will cause an arrhythmia. The abnormality of the ECG is detected and the excitatory signal is stopped. An another example, a second, ETC, signal may be designated to block the propagating of the excitatory signal. However, due to the abnormal activation, such blocking may not work and/or the application of the ETC signal itself may cause an arrhythmia.

It should be noted that in some cases, the inhibited signal might have directly caused an arrhythmia. In other cases, the signal would only have prepared the grounds for a later arrhythmia, for example, by depressing a portion of the heart for several cycles. In other case, as noted above, it is an existing arrhythmia (possibly self-limiting) that prepare the grounds for the non-excitatory signal to cause an arrhythmia (possibly non-self limiting).

Alternatively or additionally to preventing signals that are dangerous, in an exemplary embodiment of the invention, filter 104 is used to prevent ineffective signals. An ETC signal may have one or more associated templates and/or matching parameter sets that indicate conditions of lesser effectiveness. Such ineffective signals may have, for example, one or more of the following undesirable effects:

(a) weaken the heart;

(b) waste power;

(c) have a counter-desired effect (e.g., reduce contractility);

(d) undo a desired long term effect of the ETC signals (e.g., modeling); and (e) cause pain to the patient.

Optionally, the effectiveness of an ETC signal is defined parametrically, for example based on the instant level of cardiac reserve ability. Such an instant level may be provide, for example, by a model that tracks the response of the heart to previously applied ETC signals, under various conditions. Inefficient effect of an ETC signal may also be detected using non-electrical sensors, for example pressure sensors. Optionally, a pressure or a tension sensor in an earlier activated part of the heart (e.g., an earlier activated chamber) may be used to generate a trace for matching to a template, for detecting abnormal activation of the heart.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

What is claimed is:

1. Apparatus for applying a non-excitatory signal to a heart, comprising:

at least one electrode;

a power source;

a wide-field ECG sensor that receives a wide-field ECG signal containing contributions from non-local sized portions of the heart;

a controller for selectively electrifying said at least one electrode with a non-excitatory signal from said power source; and a safety filter that inhibits said electrifying responsive to said wide-field ECG signal.

2. Apparatus according to claim 1, wherein said wide-field ECG sensor detects electric field contributions from at least two heart chambers.

3. Apparatus according to claim 1, wherein said wide-field ECG sensor detects electric field contributions from an area of at least 5 cm$^2$ of the heart.

4. Apparatus according to claim 1, wherein said wide-field ECG sensor detects electric field contributions from an area of at least 15 cm$^2$ of the heart.

5. Apparatus according to claim 1, wherein said wide-field ECG sensor detects electric field contributions from at least one quarter of a heart chamber.

6. Apparatus according to claim 1, wherein said wide-field ECG sensor detects electric field contributions from at least one third of a heart chamber.

7. Apparatus according to claim 1 wherein said wide-field ECG sensor detects electric field contributions from parts of the heart that are expected to be activated prior to said electrifying.

8. Apparatus according to claim 1, wherein said wide-field ECG sensor detects electric field contributions from parts of the heart that are expected to be activated after to said electrifying.

9. Apparatus according to claim 1, wherein said wide-field ECG sensor includes at least one component shared with a sensor used for timing said electrifying.

10. Apparatus according to claim 9, wherein said wide-field ECG sensor shares said at least one electrode.

11. Apparatus according to claim 1, wherein said non-excitatory signal increases a contractility of at least a portion of said heart.

12. Apparatus according to claim 1, wherein said safety filter includes a template matcher that matches said ECG trace to at least one template.

13. Apparatus according to claim 12, wherein said template matcher matches said ECG trace to at least one template suitable for a paced heart and at least one template suitable for an unpaced heart.

14. Apparatus according to claim 12, wherein said at least one template includes at least two templates, each designated for different heart rates.

15. Apparatus according to claim 12, wherein said at least one template includes a single template suitable for multiple heart rates.

16. Apparatus according to claim 12, wherein said at least one template includes at least two templates, each designated for a different non-excitatory signal.

17. Apparatus according to claim 12, wherein said at least one template includes at least two templates, each designated for a wide-field ECG sensing area.

18. Apparatus according to claim 12, wherein said at least one template includes an ECG portion corresponding to a period between a right ventricle pacing or sensing event and a time for application of a non-excitatory signal.

19. Apparatus according to claim 12, wherein said at least one template is continuously updated.

20. Apparatus according to claim 19, wherein said at least one template is updated to be a weighted average of a current template and a current ECG signal.

21. Apparatus according to claim 19, wherein said at least one template is updated with both normal and abnormal ECG signals.

22. Apparatus according to claim 12, wherein said filter ignores templates that did not match for a considerable period of time.

23. Apparatus according to claim 1, wherein said filter prevents said electrification from starting.

24. Apparatus according to claim 1, wherein said filter stops an ongoing electrification from continuing.

25. Apparatus according to claim 1, wherein said filter is configured to prevent arrhythmia to be caused by said non-excitatory signal.

26. Apparatus according to claim 1, wherein said filter is configured to prevent inefficient non-excitatory signal to be applied to said heart.

27. Apparatus according to claim 1, wherein said wide-field ECG sensor comprises two electrode portions spaced apart at least 3 centimeters.

28. Apparatus according to claim 27, wherein said wide-field ECG sensor comprises two electrode portions spaced apart at least 5 centimeters.

29. Apparatus according to claim 27, wherein at least one of said two electrode portions is adapted to be placed distanced from the heart.

30. Apparatus according to claim 27, wherein at least one of said two electrode portions is adapted to be in contact with the heart's inner surface.

31. Apparatus according to claim 27, wherein at least one of said two electrode portions is adapted to be in contact with the heart's outer surface.

32. Apparatus according to claim 27, wherein at least one of said two electrode portions is adapted to float in the heart's volume.

33. Apparatus according to claim 27, wherein said two electrodes are mounted on a same elongate lead.

34. A method of determining if to inhibit the application of a non-excitatory signal to the heart, comprising:

detecting a non-local ECG trace;

determining if said trace indicates a normal activation of the heart; and inhibiting the application of a non-excitatory signal responsive to a negative determination of said trace.

* * * * *